US009212123B2

(12) United States Patent
Chi et al.

(10) Patent No.: US 9,212,123 B2
(45) Date of Patent: Dec. 15, 2015

(54) COSMETIC COMPOSITION OBTAINED BY ESTERIFICATION OF AMYL ALCOHOL OR AN ISOMER THEREOF AND A NATURAL VEGETABLE OIL FATTY ACID

(71) Applicant: Jun-Hong Chi, Yongin-si (KR)

(72) Inventors: Jun-Hong Chi, Yongin-si (KR); Dae Ho Bae, Hwaseong-si (KR)

(73) Assignee: Jun-Hong Chi (KR)

( * ) Notice: Subject to any disclaimer, the term of this patent is extended or adjusted under 35 U.S.C. 154(b) by 132 days.

(21) Appl. No.: 14/347,349

(22) PCT Filed: Oct. 5, 2012

(86) PCT No.: PCT/KR2012/008084
§ 371 (c)(1),
(2) Date: Mar. 26, 2014

(87) PCT Pub. No.: WO2013/055062
PCT Pub. Date: Apr. 18, 2013

(65) Prior Publication Data
US 2015/0299092 A1    Oct. 22, 2015

(30) Foreign Application Priority Data

Oct. 11, 2011  (KR) .................. 10-2011-0103370

(51) Int. Cl.
*C11C 1/00*     (2006.01)
*C07C 67/08*    (2006.01)
(Continued)

(52) U.S. Cl.
CPC . *C07C 67/08* (2013.01); *A61K 8/37* (2013.01); *A61Q 1/02* (2013.01); *A61Q 1/06* (2013.01); *A61Q 19/00* (2013.01); *C07C 69/24* (2013.01); *C07C 69/533* (2013.01); *C07C 69/587* (2013.01)

(58) Field of Classification Search
CPC ...... C07C 67/08; C07C 69/24; C07C 69/533; C07C 69/587; A61K 8/37; A61Q 1/02; A61Q 1/06; A61Q 19/00
USPC ........................................... 554/170; 514/549
See application file for complete search history.

(56) References Cited

U.S. PATENT DOCUMENTS 6,579,516 B1 * 6/2003 Mansouri ................. A61K 8/24
                                                                424/401
2009/0220437 A1 * 9/2009 Leber ...................... C11B 1/025
                                                                424/59

FOREIGN PATENT DOCUMENTS

JP       10158117        6/1998
JP       10158117 A  *  6/1998
(Continued)

OTHER PUBLICATIONS

International Search Report—PCT/KR2012/008084 dated Mar. 22, 2013.

*Primary Examiner* — Deborah D Carr
(74) *Attorney, Agent, or Firm* — Cantor Colburn LLP (57) ABSTRACT

Disclosed is a cosmetic composition containing, as an active ingredient, an ester oil obtained by the bonding and esterification of amyl alcohol or an isomer thereof and a fatty acid derived from a natural vegetable oil such as olive oil or coconut oil. The ester oil increases the viscosity and imparts stability to cosmetics while also having a far better moisturizing ability and a lighter feeling in use than silicone oil, and the invention therefore allows a naturally derived ester oil, which is relatively friendly to the human body, to be used as a fundamental base component of a cosmetic composition, in complete or partial substitution for silicone oil which has been used on account of the shortcomings of existing synthetic ester oils.

11 Claims, 6 Drawing Sheets

(51) Int. Cl.
*C07C 69/24* (2006.01)
*C07C 69/533* (2006.01)
*C07C 69/587* (2006.01)
*A61K 8/37* (2006.01)
*A61Q 19/00* (2006.01)
*A61Q 1/02* (2006.01)
*A61Q 1/06* (2006.01)

(56) References Cited

FOREIGN PATENT DOCUMENTS

| | | | |
|---|---|---|---|
| JP | 2009019049 | | 1/2009 |
| JP | 2009019049 A | * | 1/2009 |
| KR | 1020050069835 | | 7/2005 |

* cited by examiner

COSMETIC COMPOSITION OBTAINED BY ESTERIFICATION OF AMYL ALCOHOL OR AN ISOMER THEREOF AND A NATURAL VEGETABLE OIL FATTY ACID

TECHNICAL FIELD

The present invention relates to an esterified product obtained by mixing and esterification of amyl alcohol or an isomer thereof with fatty acids derived from natural vegetable oil such as olive oil or coconut oil. Particularly, the present invention relates to a cosmetic composition using the esterified product as a base oil component contained fundamentally in formulating a cosmetic agent.

BACKGROUND ART

In general, skin oil such as sebum is present on the skin surface besides moisture, and forms a sebum coating in the state of emulsion to cover and protect the skin or hair. The chemical composition of sebum forming such a sebum coating is very complex and includes free fatty acids, higher alcohols, higher hydrocarbons or other components forming oily substances, besides various oily substances. Thus, it is preferred that materials of a cosmetic agent are close to the oily substances present physiologically on the skin surface.

Therefore, oily materials are important ingredients of a cosmetic agent in addition to aqueous materials. Such oily materials may be classified into fat and oil, wax, higher hydrocarbons and synthetic esters disclosed herein, depending on the chemical structure or property thereof.

The synthetic ester oil used as a raw material of a cosmetic agent is provided for the purpose of manifesting the advantages of natural esters such as fat and oil and wax and improving the disadvantages thereof. Use of such synthetic ester oil is increasingly in demand as a substitute for the conventional silicone.

According to the related art, there has been generally used a cosmetic agent which contains liquid oil, such as paraffin, esters, higher alcohols or glycerides, to provide softness, smoothness, emollient effect, or the like. However, such a cosmetic agent is disadvantageous in that it causes an oily and sticky feel and oil coating-like appearance. Thus, in order to reduce an oily and sticky feel and oil coating-like appearance, silicone oil such as dimethylpolysiloxane is incorporated to the cosmetic agent in the art. Korean Patent Laid-Open No. 2005-0069835 discloses a hydrated type cosmetic composition using a silicone base, which utilizes a silicone crosslinked polymer to incorporate a larger amount of aqueous phase, has no preservative, and can be stored for a long time.

However, while silicone oil is spread lightly and has excellent smoothness and water repellency, it has poor compatibility with hydrocarbon-based liquid oil. In addition, since silicone oil has low surface tension, it diffuses rapidly and thus shows low durability.

DISCLOSURE

Technical Problem

A technical problem to be solved by the present invention is to provide a cosmetic composition including novel ester oil that has light spreadability, high smoothness and water repellency at least equal to silicone oil, while solving the problems of an oily and sticky feel and oil coating-like appearance occurring in liquid oil such as ester.

Technical Solution

In one general aspect, there is provided a cosmetic composition including, as an active ingredient, ester oil obtained by mixing and esterification of amyl alcohol or an isomer thereof with fatty acids derived from natural vegetable oil.

According to an embodiment, the isomer may be any one selected from the group consisting of 3-methyl-1-butanol (isoamyl alcohol), 2-methyl-1-butanol, 2,2-dimethyl-1-propanol, 3-pentanol, 2-pentanol, 3-methyl-2-butanol, and 2-methyl-2-butanol.

According to another embodiment, the natural vegetable oil may be any natural vegetable oil capable of extraction of fatty acids thereof, and preferred natural vegetable oil includes olive oil or coconut oil.

According to still another embodiment, the fatty acids derived from olive oil may be at least one selected from the group consisting of palmitic acid, palmitoleic acid, stearic acid, oleic acid, linoleic acid and linolenic acid. In addition, the fatty acids derived from coconut oil may be at least one selected from the group consisting of caprylic acid, capric acid, lauric acid, myristic acid, palmitic acid, stearic acid and oleic acid.

According to still another embodiment, the fatty acids derived from natural vegetable oil may be any fatty acid obtained from natural vegetable oil such as coconut or oil olive oil by any extraction method known to those skilled in the art. Preferably, the fatty acid is a mixture of fatty acids extracted from natural vegetable oil by using a high-temperature high-pressure method.

According to still another embodiment, the ester oil may be at least one isoamyl olivate selected from the following Structural Formulae 8 to 13 (see the formulae represented hereinafter) and at least one isoamyl cocoate selected from the following Structural Formulae 14 to 30 (see the formulae represented hereinafter).

According to still another embodiment, the cosmetic composition preferably has a skin moisturizing effect and an effect of thickening a cosmetic agent. According to an example of the present invention, it is demonstrated that the ester oil disclosed herein has a higher moisturizing effect as compared to the conventional silicone oil and light feel of use, and increases the viscosity of a cosmetic agent, thereby imparting stability thereto.

In another general aspect, there is provided a cosmetic product including, as base oil, the cosmetic composition including the ester oil disclosed herein as an active ingredient.

Base oil is a fundamental ingredient of a cosmetic product, and forms a skin coating when it is mixed with other cosmetic compositions and applied to the skin, thereby providing a moisture-retaining and skin moisturizing effect.

According to an embodiment, the cosmetic product may be any one including the cosmetic composition. Preferably, the cosmetic product is lotion, cream, serum, foundation, sun cream, BB cream, makeup base, lip gloss or lipstick.

The present invention relates to an esterified product of amyl alcohol or an isomer thereof with different types of fatty acids derived from coconut oil and olive oil that belong to natural vegetable oil. In still another general aspect, there is provided a cosmetic composition using the esterified product as a base of oil formulation used fundamentally in formulating a cosmetic agent, instead of silicone oil.

Amyl alcohol is represented by a molecular formula of $C_5H_{11}OH$ and has seven types of isomers. Amyl alcohols and isomers thereof are shown in the following Table 1.

TABLE 1

| IUPAC Name | Structural Formula |
|---|---|
| 1-pentanol (amyl alcohol) | ~~~OH |
| 3-methyl-1-butanol (isoamyl alcohol) | (structure)OH |
| 2-methyl-1-butanol | (structure)OH |
| 2,2-dimethyl-1-propanol | (structure)OH |
| 3-pentanol | (structure)OH |
| 2-pentanol | (structure)OH |
| 3-methyl-2-butanol | (structure)OH |
| 2-methyl-2-butanol | (structure)OH |

In the present invention, amyl alcohol isomers have higher oily characteristics (oleophilic properties) than amyl alcohol, and thus are more preferred. Most preferably, among such amyl alcohol isomers, 3-methyl-1-butanol (isoamyl alcohol) is used to prepare the ester oil according to the present invention. Amyl alcohol is hydrophilic but isoamyl alcohol shows stronger oily characteristics while it is converted to the isomeric form. In addition, unlike the oily alcohol, isoamyl alcohol has a small number of carbon atoms and shows a soft feel of use, and thus provides viscosity comparable to the viscosity of silicone oil such as cyclomethicone.

Each of amyl alcohol and isomers thereof is subjected to esterification by using fatty acids derived from coconut oil and olive oil as natural vegetable oil to obtain synthetic ester oil for use in a cosmetic composition.

Some methods for preparing fatty acids through hydrolysis of fat and oil such as natural vegetable oil including coconut oil and olive oil are known to those skilled in the art, and include a high-temperature high-pressure method, alkali decomposition method, alcoholysis method and enzymatic hydrolysis method.

In the case of an alkali decomposition method, a significant amount of energy is required regardless of the type (batch process or continuous process). Particularly, an alkali decomposition method includes reacting fat and oil with caustic soda or caustic potash to perform saponification, and treating the resultant soap with an acid such as hydrochloric acid to obtain fatty acids and glycerol. Thus, it provides a low production yield relative to energy consumption.

In addition, an alcoholysis method requires a large-scale complex system and equipment and a broad space. It also requires a system for recovering alcohol and requires consumption of a significant amount of energy. Moreover, an alcoholysis method entails a risk of explosion.

Further, in the case of an enzymatic decomposition method that has been conducted recently, a mild condition, simple system and equipment and low energy consumption are required. However, it still provides a low yield.

Under these circumstances, according to the present invention, fatty acids are obtained by using a high-temperature high-pressure method to prepare the ester oil. When using the high-temperature high-pressure method, fatty acids are obtained in a yield of 95-99% from coconut oil and olive oil.

An esterification process of amyl alcohol or an isomer thereof with fatty acids derived from coconut oil and olive oil is the same as the conventionally commercialized dehydration condensation process. Although any catalyst such as a chemical catalyst, metal catalyst or enzyme catalyst may be used, a chemical catalyst is used to carry out the esterification process according to the present invention.

Advantageous Effects

As described above, the ester oil according to the embodiments of the present invention has a higher moisturizing effect than silicone oil, shows a light feel of use and increases the viscosity of a cosmetic agent to impart stability thereto. Therefore, the ester oil can partially or totally substitute silicone oil commercialized due to the disadvantages of the conventional synthetic ester oil, and thus allows a cosmetic composition to have more human-friendly naturally occurring ester oil as a base ingredient.

BEST MODE

Exemplary embodiments now will be described more fully hereinafter with reference to the accompanying drawings, in which exemplary embodiments are shown. This disclosure may, however, be embodied in many different forms and should not be construed as limited to the exemplary embodiments set forth therein.

Example 1

Preparation of Olive Oil-Derived Fatty Acids

Figure 1:
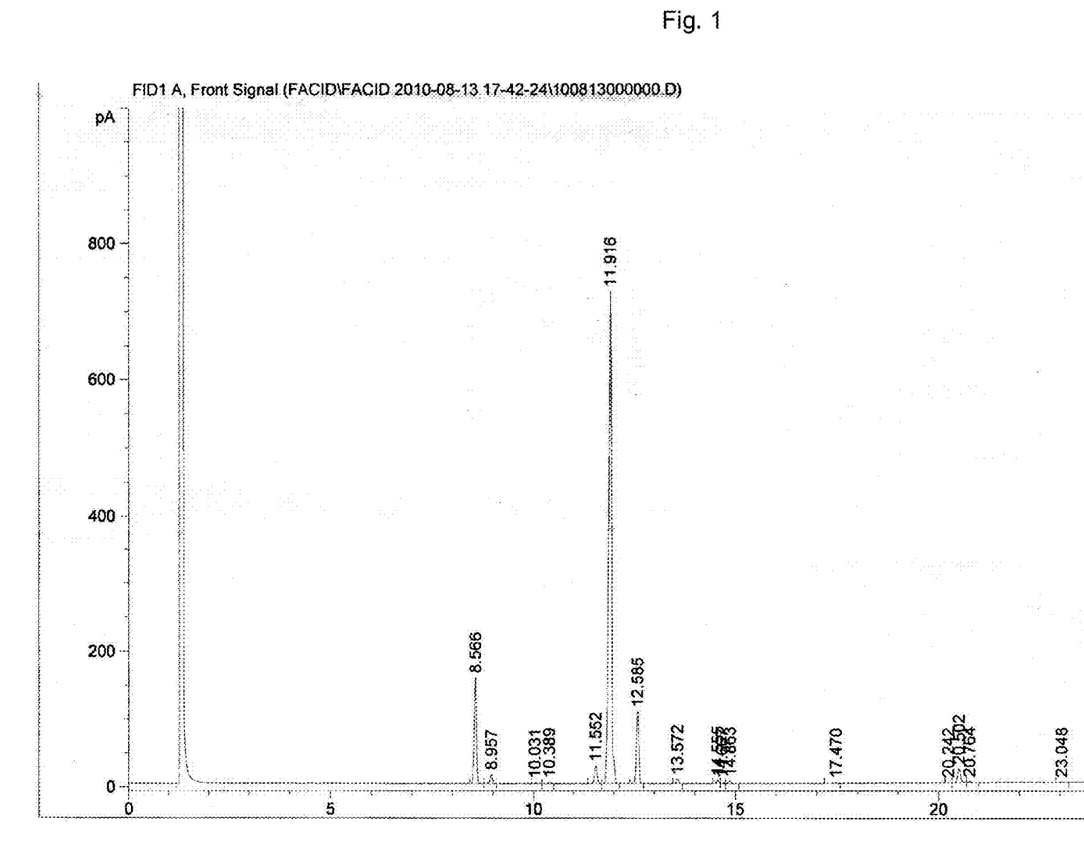
FIG. 1 is a gas chromatography analysis chart illustrating the composition of fatty acids of olive oil.

First, olive oil is agitated with distilled water at the same weight ratio. Then, the reaction mixture is introduced to SUS316L reactor resistant against high temperature and high pressure, and subjected to a high-temperature and high-pressure process at 150-200° C. for 5-10 hours while maintaining 10-20 atm. After the completion of the reaction, the reaction mixture is allowed to stand and the lower layer containing a mixture of distilled water with glycerin is discharged and removed, while the upper fatty acid layer is recovered. The upper fatty acid layer still contains distilled water and glycerin, and thus subjected to dehydration under reduced pressure to remove water completely. In addition, the upper fatty acid layer is subjected to washing with water and dehydration twice or three times to remove the remaining glycerin and water completely. After that, fatty acids are obtained in a yield of 95-99%. The composition of the fatty acids of olive oil obtained as described above is analyzed by gas chromatography and the analysis chart is shown in FIG. 1.

The composition of different types of fatty acids derived from olive oil in the manner as described above is shown in the following Table 2.

TABLE 2

| Composition of fatty acids derived from olive oil | |
|---|---|
| Oleic acid | 70.0-80.0% |
| Linoleic acid | 6.0-10.0% |
| Linolenic acid | 0.5-2.0% |
| Palmitic acid | 10.0-12.0% |
| Palmitoleic acid | 0.5-2.0% |
| Stearic acid | 2.0-4.0% |
| Others | 0.5-3.0% |

However, the composition of fatty acids derived from olive oil that may be used in the present invention is not limited to Table 2. Typical fatty acids forming olive oil that may be used in the present invention are palmitic acid, palmitoleic acid, stearic acid, oleic acid, linoleic acid and linolenic acid represented by the following Structural Formulae 1-6.

[Stuctural Formula 1]

Palmitic acid

[Stuctural Formula 2]

Palmitoleic acid

[Stuctural Formula 3]

Stearic acid

[Stuctural Formula 4]

Oleic acid

[Stuctural Formula 5]

Linoleic acid

[Stuctural Formula 6]

Linolenic acid

Example 2

Preparation of Coconut Oil-Derived Fatty Acids

Figure 2:
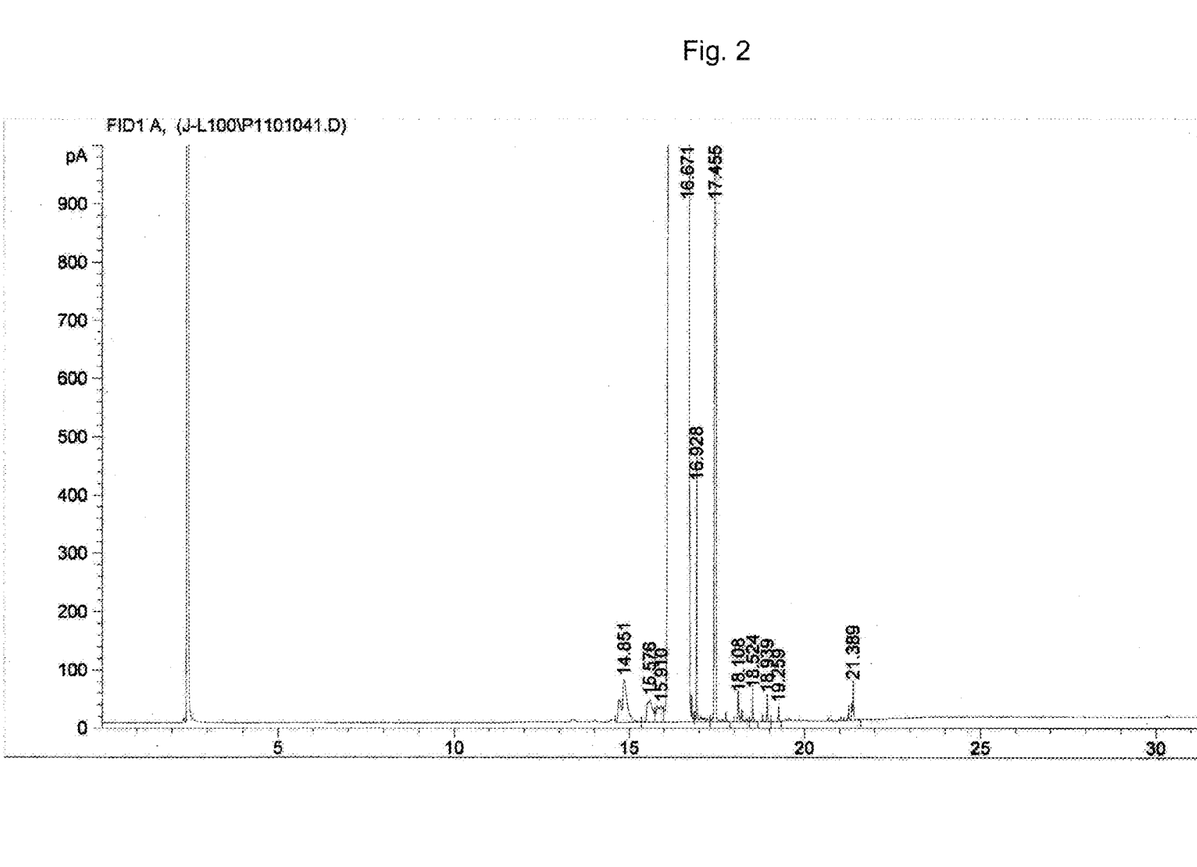
FIG. 2 is a gas chromatography analysis chart illustrating the composition of isoamyl olivate which is a type of ester oil according to the present invention.

First, coconut oil is agitated with distilled water at the same weight ratio. Then, the reaction mixture is introduced to SUS316L reactor resistant against high temperature and high pressure, and subjected to a high-temperature and high-pressure process at 150-200° C. for 5-10 hours while maintaining 10-20 atm. After the completion of the reaction, the reaction mixture is allowed to stand and the lower layer containing a mixture of distilled water with glycerin is discharged and removed, while the upper fatty acid layer is recovered. The upper fatty acid layer still contains distilled water and glycerin, and thus subjected to dehydration under reduced pressure to remove water completely. In addition, the upper fatty acid layer is subjected to washing with water and dehydration twice or three times to remove the remaining glycerin and water completely. After that, fatty acids are obtained in a yield of 95-99%. The composition of the fatty acids of coconut oil obtained as described above is analyzed by gas chromatography and the analysis chart is shown in FIG. 2.

The composition of different types of fatty acids derived from coconut oil in the manner as described above is shown in the following Table 3.

TABLE 3

| Composition of fatty acids derived from coconut oil | |
|---|---|
| Caprylic acid | 5-9% |
| Capric acid | 5-8% |
| Lauric acid | 38-48% |
| Myristic acid | 10-18% |
| Palmitic acid | 5-9% |
| Stearic acid | 1-4% |
| Oleic acid | 5-9% |

However, the composition of fatty acids derived from coconut oil that may be used in the present invention is not limited to Table 3. Typical fatty acids forming coconut oil that may be used in the present invention are caprylic acid, capric acid, lauric acid, myristic acid, palmitic acid, stearic acid and oleic acid represented by the following Structural Formulae 7-13.

[Structural Formula 7] Caprylic acid
[Structural Formula 8] Capric acid
[Structural Formula 9] Lauric acid
[Structural Formula 10] Myristic acid
[Structural Formula 11] Palmitic acid
[Structural Formula 12] Stearic acid

[Structural Formula 13]

Oleic acid

Example 3

Preparation of Ester Oil 1

The olive oil-derived fatty acids obtained from Example 1 and isoamyl alcohol represented by the following Structural Formula 14 are subjected to esterification to obtain ester oil.

[Structural Formula 14]

Isoamyl alcohol

The esterification is carried out as follows. First, 3-methyl-1-butanol, an isomer of amyl alcohol, is mixed with the previously formed fatty acids of olive oil at a molar ratio of 1-2:1. Then, an acid catalyst is introduced to the resultant mixture in an amount of 0.1-1 parts by weight based on the weight of fatty acids and mixed thoroughly.

The mixture is dehydrated under nitrogen at 120-200° C. for 5-10 hours. The reaction is continued while the water produced through the esterification is separated by a cooling condenser.

After the completion of the reaction, crude ester is subjected to distillation under reduced pressure to remove the remaining 3-methyl-1-butanol (isoamyl alcohol), and the unreacted fatty acids are removed by neutralization with alkali. Finally, the resultant product is washed with distilled water 1-3 times to remove the residual fatty acid soap and sludge, and then subjected to dehydration under reduced pressure to remove the remaining water completely, thereby providing the ester oil according to the present invention.

The esterified product of the mixture of isoamyl alcohol with olive oil-derived fatty acids is a mixture of the following Structural Formulae 15-20, and provides the unique physical properties and silicone-like advantages when it is present as mixed fatty acid esters having the non-modified composition of fatty acids of olive oil as it is. The chart illustrating the overall composition analyzed by gas chromatography is shown in FIG. 2.

[Structural Formula 15]

Isoamyl palmitate

[Structural Formula 16]

Isoamyl palmitoleate

[Structural Formula 17]

Isoamyl stearate

[Structural Formula 18]

Isoamyl oleate

[Structural Formula 19]

Isoamyl linoleate

[Structural Formula 20]

Isoamyl linolenate

Example 4

Preparation of Ester Oil 2

The coconut oil-derived fatty acids obtained from Example 2 and isoamyl alcohol are subjected to esterification to obtain ester oil.

The esterification is carried out as follows. First, 3-methyl-1-butanol, an isomer of amyl alcohol, is mixed with the previously formed fatty acids of coconut oil at a molar ratio of 1-2:1. Then, an acid catalyst is introduced to the resultant mixture in an amount of 0.1-1 parts by weight based on the weight of fatty acids and mixed thoroughly.

The mixture is dehydrated under nitrogen at 120-200° C. for 5-10 hours. The reaction is continued while the water produced through the esterification is separated by a cooling condenser.

After the completion of the reaction, crude ester is subjected to distillation under reduced pressure to remove the remaining 3-methyl-1-butanol (isoamyl alcohol), and the unreacted fatty acids are removed by neutralization with alkali. Finally, the resultant product is washed with distilled water 1-3 times to remove the residual fatty acid soap and sludge, and then subjected to dehydration under reduced pressure to remove the remaining water completely, thereby providing the ester oil according to the present invention.

Figure 3:
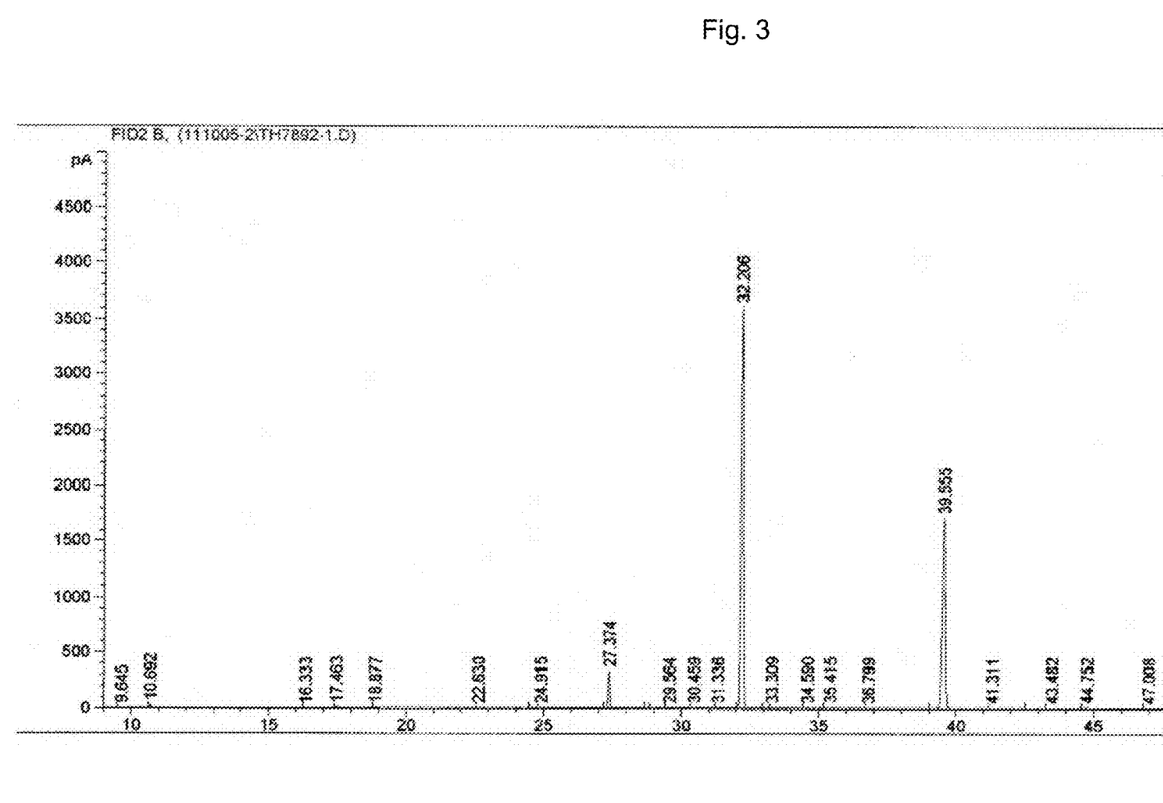
FIG. 3 is a gas chromatography analysis chart illustrating the composition of fatty acids of coconut oil.
Figure 4:
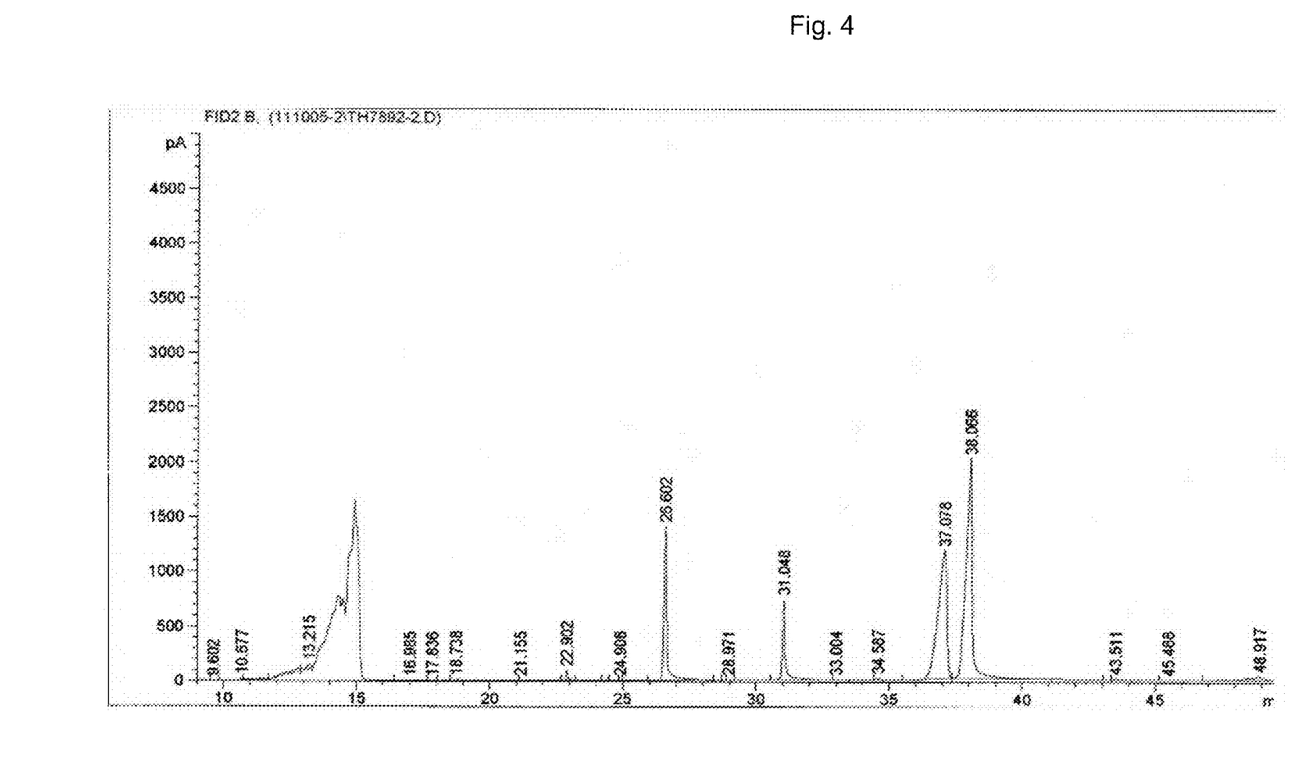
FIG. 4 is a gas chromatography analysis chart illustrating the composition of isoamyl cocoate which is a type of ester oil according to the present invention.

The esterified product of the mixture of isoamyl alcohol with coconut oil-derived fatty acids is a mixture of the following Structural Formulae 21-27, and provides the unique physical properties and silicone-like advantages when it is present as mixed fatty acid esters having the non-modified composition of fatty acids of coconut oil as it is. The chart illustrating the overall composition analyzed by gas chromatography is shown in FIG. 3.

[Structural Formula 21]

Isoamyl caprylate

[Structural Formula 22]

Isoamyl caprate

[Structural Formula 23]

Isoamyl laurate

[Structural Formula 24]

Isoamyl myristate

[Structural Formula 25]

Isoamyl palmitoleate

[Structural Formula 26]

Isoamyl stearate

[Structural Formula 27]

Isoamyl oleate

The ester oil obtain according to the present invention is human-friendly oil having a light and soft feel of use, and can provide a feel of use with higher quality due to the composition of mixed fatty acids derived from coconut oil and olive oil as natural vegetable oil, as compared to a single fatty acid or optionally formulated fatty acids.

Example 5

Test of Measuring Properties of Ester Oil

The fatty acid ester oil provided in the form of a combination of Structural Formulae 8-13 as described in Example 3 solves the problems of oily and sticky feel and oily coating-like appearance occurring in the conventional synthetic ester oil, while showing the advantages of the conventional silicone oil, including light spreadability and high smoothness and water repellency. In addition, the fatty acid ester oil overcomes the disadvantage of silicone oil, i.e., degradation of compatibility with hydrocarbon-based liquid oil. Further, the fatty acid oil solves the problem of low durability due to the low surface tension and rapid diffusion, thereby providing a significantly improved cosmetic composition.

Particularly, the ester oil of Example 3 has the properties as shown in the following Table 4.

TABLE 4

| Item | Properties |
| --- | --- |
| Appearance | Colorless and transparent, or pale yellow liquid |
| Acid value | 2 mgKOH/g or less |
| Peroxide value | 2 meq/kg or less |
| Saponification value | 170-210 |
| Viscosity | 1-10 cps(20-25° C.) |
| Refractive index | 1.4200-1.4900 |
| Water content | 0.1% or less |

When the ester oil of Example 3 has the composition of a mixture of Structural Formulae 8-13 and the properties as shown in Table 4, it shows the physical properties according to the present invention. Particularly, while the ester oil has the advantages of silicone oil, including spreadability, smoothness and water repellency, which, otherwise, cannot be provided by the conventional ester oil, it solves the problem of poor durability occurring in silicone oil due to the high diffusibility and provides compatibility with hydrocarbon-based liquid oil.

In addition, when the ester oil of Example 4 has the properties as shown in Table 5, it shows the physical properties according to the present invention. Particularly, while the ester oil has the advantages of silicone oil, including spreadability, smoothness and water repellency, which, otherwise, cannot be provided by the conventional ester oil, it solves the problem of poor durability occurring in silicone oil due to the high diffusibility and provides compatibility with hydrocarbon-based liquid oil.

TABLE 5

| Item | Properties |
| --- | --- |
| Appearance | Colorless and transparent, or pale yellow liquid |
| Acid value | 2 mgKOH/g or less |
| Peroxide value | 2 meq/kg or less |
| Saponification value | 190-250 |
| Viscosity | 1-10 cps(20-25° C.) |
| Refractive index | 1.4200-1.4900 |
| Water content | 0.1% or less |

To compare the moisturizing effect of a typical example of silicone oil (Cyclomethicone) according to the related art with that of the ester oil according to the present invention, Corneometer CM820 and Tewameter TM210, each of which is available from CK Electronic Co. (Germany), are used to perform evaluation. For reference, caprylic/capric triglyceride, squalane and isononyl isononanoate currently used as universal moisturizing agents in cosmetic products are evaluated.

Before evaluating the skin moisturizing effect, preparation is made as follows.

To evaluate the skin water content provided by cream, ten subjects of twenties are selected and allowed to be stabilized under a constant-temperature constant-humidity condition (temperature 25-30° C., relative humidity 40-60%) for a predetermined time (at least 1 hour). Then, cautions are given to them and test content forms are received from them. For the test, cream is applied to the subjects and measurement is carried out 20 minutes after the application.

The test is carried out as follows.

First, cream is applied to the inside portion of an arm and the water content is determined. The water content is measured by using Corneometer CM820 and the resultant capacitance value is converted into an arbitrary capacitance unit (A.U.) of between 0 and 120.

All of the tests are repeated three times, and statistical analysis is performed by the student's t-test at a significance level of 5%. The results of skin moisture capacities (A.U.) of the ester oil according to the present invention and the other four types of samples are shown in FIG. 5.

Figure 5:
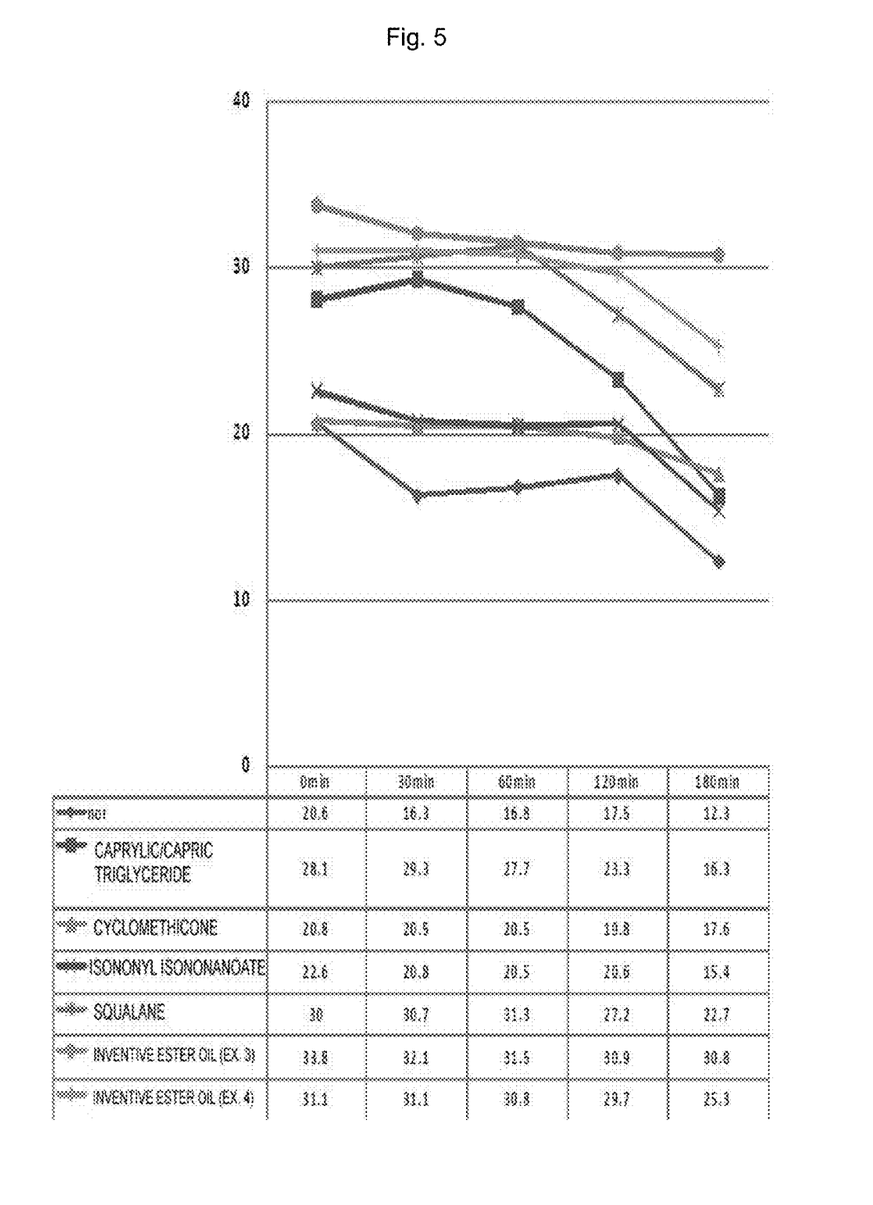
FIG. 5 is a graph illustrating the measurement of skin moisturizing effect of isoamyl olivate which is a type of ester oil according to the present invention.

As can be seen from the results of FIG. 5, the ester oil according to the present invention has a higher skin moisturizing effect as compared to the other moisturizing agents. Therefore, when using the ester oil according to the present invention in a cosmetic composition, it is possible to enhance the moisturizing effect to 1.5-2 times of the moisturizing effect of the conventional composition.

In addition to the comparison of moisturizing effect, the ester oil according to the present invention is compared with the typical moisturizing agents in terms of the effect of increasing the viscosity of a cosmetic agent.

In general, when oil has high viscosity, the cosmetic agent using the oil shows increased viscosity. On the other hand, when oil has low viscosity, the cosmetic agent using the oil shows decreased viscosity. Thus, it is thought that the viscosity of a cosmetic agent is closely related to the stability of a cosmetic agent formulation.

As can be seen from the results of viscosity measurement as described hereinafter, the ester oil according to the present invention has a light feel of use and increases the viscosity of a cosmetic agent formulation, and thus imparts stability to a cosmetic agent. In other words, when a cosmetic agent is prepared by using the ester oil according to the present invention, the cosmetic agent has increased viscosity, but the viscosity that the ester oil originally has is low and the cosmetic agent shows a significantly light feel of use.

Particularly, when the ester oil according to the present invention is compared with cyclomethicone having a similar viscosity, the ester oil shows a significantly high thickening effect as demonstrated by an increase in viscosity of cosmetic formulation corresponding to 1.7 times on the basis of cyclomethicone.

Figure 6:
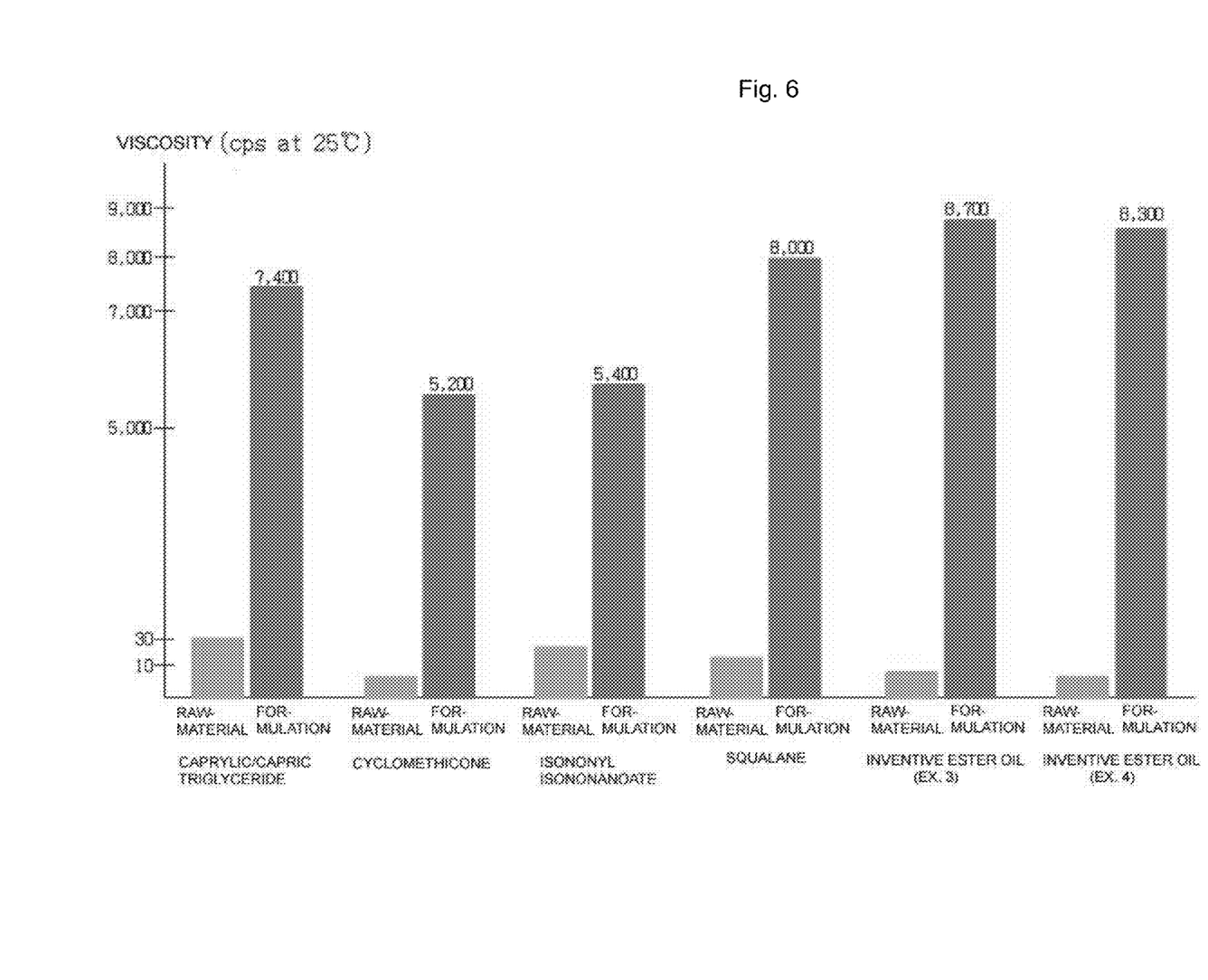
FIG. 6 is a graph illustrating the measurement of thickening effect of isoamyl olivate which is a type of ester oil according to the present invention.

The above results are shown in FIG. 6. Each viscosity value is determined by using Brookfield LVT with spindle No. 4 under 30 rpm, after each formulation is stored in a constant-temperature bath at 25° C. for 1 day while maintaining the temperature. The cosmetic agent formulations used for the viscosity measurement are shown in the following Table 6.

TABLE 6

| | Caprylic/capric triglyceride | Cyclomethicone | Isononyl isononanoate | Squalane | Inventive ester oil |
| --- | --- | --- | --- | --- | --- |
| Sorbitan olivate/ceteary olivate | 5 | 5 | 5 | 5 | 5 |
| Glycerin | 2 | 2 | 2 | 2 | 2 |
| Xanthan gum | 0.3 | 0.3 | 0.3 | 0.3 | 0.3 |
| Preservative | 0.3 | 0.3 | 0.3 | 0.3 | 0.3 |
| Ion exchange water | 84.9 | 84.9 | 84.9 | 84.9 | 84.9 |
| Corresponding Moisturizing agent | 7.5 | 7.5 | 7.5 | 7.5 | 7.5 |
| Total | 100 | 100 | 100 | 100 | 100 |

The above formulation is introduced to a cosmetic composition in an amount of 1-50 parts by weight based on 100 parts by weight of the total cosmetic composition.

Hereinafter, the present invention will be explained in more detail with reference to some cosmetic agent formulation examples. However, the scope of the present invention is not limited to the following examples.

Cosmetic Agent Formulation Example 1

In this example, the ester oil according to the present invention is used to a formulation of ultra-moisturizing lotion. The formulation is as follows.

As aqueous phase materials, purified water is mixed well with 2 parts by weight of cetearyl olivate and sorbitan olivate, 2 parts by weight of glycerin, 3 parts by weight of 1,3-butylene glycol and 0.02 parts by weight of disodium EDTA as emulsifiers.

Next, 0.2 parts by weight of xanthan gum is dispersed sufficiently to purified water and introduced to the aqueous phase materials.

Then, as oil phase materials, 20 parts by weight of the ester oil according to the present invention is introduced to 0.5 parts by weight of cetearyl alcohol, 1 part by weight of glyceryl stearate and 10 parts by weight of neopentylglycol diheptanoate and allowed to be dissolved at about 75° C. The resultant mixture is introduced gradually to the aqueous phase materials. After the introduction, the materials are mixed by a homomixer for about 10 minutes. Then, at about 65° C., 0.08 parts by weight of Carbopol 941 is dispersed well into purified water and added to the mixture. Finally, 0.08 parts by weight of triethanolamine is introduced to the mixture to perform stabilization.

After cooling the resultant formulation gradually at room temperature, ultra-moisturizing lotion using the ester oil according to the present invention is obtained.

Cosmetic Agent Formulation Example 2

In this example, the ester oil according to the present invention is used to a formulation of ultra-moisturizing cream. The formulation is as follows.

As aqueous phase materials, purified water is mixed well with 2 parts by weight of cetearyl olivate and sorbitan olivate, 2 parts by weight of glycerin, 3 parts by weight of 1,3-butylene glycol and 0.02 parts by weight of disodium EDTA as emulsifiers.

Next, 0.2 parts by weight of xanthan gum is dispersed sufficiently to purified water and introduced to the aqueous phase materials.

Then, as oil phase materials, 25 parts by weight of the ester oil according to the present invention is introduced to 1.2 parts by weight of cetearyl alcohol, 1 part by weight of glyceryl stearate, 10 parts by weight of neopentylglycol diheptanoate, 1 part by weight of butter and 0.8 parts by weight of multiwax and allowed to be dissolved at about 75° C. The resultant mixture is introduced gradually to the aqueous phase materials. After the introduction, the materials are mixed well by a homomixer.

Then, at about 65° C., 0.06 parts by weight of Carbopol 940 is dispersed well into purified water and added to the formulation. Finally, 0.06 parts by weight of triethanolamine is introduced to the mixture to perform stabilization.

After cooling the resultant formulation gradually at room temperature, ultra-moisturizing cream using the ester oil according to the present invention is obtained.

Cosmetic Agent Formulation Example 3

In this example, the ester oil according to the present invention is used to a formulation of cream. The formulation is as follows.

As aqueous phase materials, purified water is mixed well with 2 parts by weight of cetearyl olivate and sorbitan olivate, 5 parts by weight of Glycereth-26, 2 parts by weight of 1,3-butylene glycol and 0.2 parts by weight of triethanolamine.

Then, as oil phase materials, 5 parts by weight of the ester oil according to the present invention is introduced to 1.5 parts by weight of cetearyl alcohol, 0.5 parts by weight of glyceryl stearate, 0.5 parts by weight of KF-96 6CS (Dimethicone), 5 parts by weight of caprylic/capric triglyceride and 5 parts by weight of squalane and allowed to be dissolved at about 75° C. The resultant mixture is introduced gradually to the aqueous phase materials, followed by agitation.

Then, at about 65° C., 20 parts by weight of 1% (w/w) aqueous solution of Carbopol 940 is introduced to the mixture of aqueous phase materials with oil phase materials, followed by agitation.

After cooling the resultant formulation gradually at room temperature, cosmetic cream using the ester oil according to the present invention is obtained.

Cosmetic Agent Formulation Example 4

In this example, the ester oil according to the present invention is used to a formulation of serum. The formulation is as follows.

As aqueous phase materials, purified water, 3 parts by weight of glycerin and 0.2 parts by weight of triethanolamine are heated to about 70° C. and mixed by a homomixer.

Then, as oil phase materials, 2 parts by weight of the ester oil according to the present invention is introduced to 1.5 parts by weight of cetearyl olivate and sorbitan olivate, 0.5 parts by weight of Arlacel 165, 1.5 part by weight of butter, 1 part by weight of KF-96 6CS (Dimethicone) and 4 parts by weight of cyclohexasiloxane and allowed to be dissolved at about 75° C. The resultant mixture is introduced gradually to the aqueous phase materials.

Then, the resultant mixture is agitated well by a homomixer at about 75° C. At about 65° C., 20 parts by weight of 1% (w/w) aqueous solution of Carbopol 940 is introduced to the mixture, followed by agitation.

After cooling the resultant formulation gradually at room temperature, serum using the ester oil according to the present invention is obtained.

Cosmetic Agent Formulation Example 5

In this example, the ester oil according to the present invention is used to a formulation of oil in water foundation. The formulation is as follows.

As oil phase materials, 4 parts by weight of the ester oil is added to 0.5 parts by weight of disteadimonium hectorite, 0.5 parts by weight of ozokerite, 1 part by weight of sorbitan olivate, 3 parts by weight of cetyl dimethicone copolyol, 4 parts by weight of octylmethoxy cinnamate, 1 part by weight of trimethylsiloxy silicate and 2 parts by weight of phenyltrimethicone, followed by heating and mixing at about 72° C. Then, the resultant colored mixture is dispersed into and added to 24.7 parts by weight of cyclohexasiloxane.

As aqueous phase materials, 1,3-butylene glycol and purified water are mixed in an adequate amount and stored at room temperature.

The aqueous phase materials are added gradually to the oil phase materials under agitation. After that, the resultant mixture is agitated for about 30 minutes to obtain a foundation product using the ester oil according to the present invention.

Cosmetic Agent Formulation Example 6

In this example, the ester oil according to the present invention is used to a formulation of sun cream. The formulation is as follows.

As oil phase materials, sorbitan olivate, disteadimonium hectorite, cetyl dimethicone copolyol, ethylhexyl methoxy cinnamate, isoamyl-p-methoxy cinnamate, cyclohexasiloxane, UV protecting agent and the ester oil according to the present invention are mixed in an adequate amount, and the resultant colored mixture is heated to about 75° C.

As aqueous phase materials, propylene glycol and purified water are mixed in an adequate amount and the mixture is heated to about 75° C.

The aqueous phase materials are introduced to the oil phase materials, followed by agitation. After that, the resultant mixture is agitated while it is cooled gradually to obtain a sun cream product using the ester oil according to the present invention.

Cosmetic Agent Formulation Example 7

In this example, the ester oil according to the present invention is used to a formulation of BB cream. The formulation is as follows.

As oil phase materials, bees wax, Vaseline, sorbitan olivate, cetyl dimethicone copolyol, liquid paraffin, cetyl ethylhexanoate and the ester oil according to the present invention are mixed in an adequate amount, and the resultant mixture is heated and agitated at about 72° C. To the resultant mixture, octyldodecanol, aluminum stearate aerosil and silica dimethyl silicate are added in a small amount.

As aqueous phase materials, glycerin and purified water are mixed and stored at room temperature.

Then, the aqueous materials are introduced gradually to the oil phase materials under agitation.

A color base in further introduced thereto and the resultant mixture is agitated for about 30 minutes to obtain a BB cream product using the ester oil according to the present invention.

Cosmetic Agent Formulation Example 8

In this example, the ester oil according to the present invention is used to a formulation of makeup base. The formulation is as follows.

As aqueous phase materials, purified water and glyceryl caprylate are mixed in a small amount and the resultant mixture is heated and agitated at 75° C.

To the heated aqueous phase materials, cetearyl olivate and sorbitan olivate are added in an adequate amount and agitated until they are dissolved completely.

Then, a mixture of cetyl palmitate with sorbitan palmitate, sunflower oil, caprylic/capric triglyceride and the ester oil according to the present invention are added in an adequate amount, followed by agitation.

Then, a color base is added thereto and dispersed therein completely, and the corresponding oil is added and agitated homogeneously. After introducing the additives at about 40-50° C., a makeup base product using the ester oil according to the present invention is obtained.

Cosmetic Agent Formulation Example 9

In this example, the ester oil according to the present invention is used to a formulation of lip gloss. The formulation is as follows.

Polybutene, sorbitan olivate, oleyl alcohol, triethyl hexanoin, meadowfoam seed oil, polyglyceryl-2-triisostearate, color base and fragrance are mixed, and the ester oil according to the present invention is introduced to the resultant mixture in a predetermined amount and dissolved therein at 75-80° C.

The materials are dispersed by using a homomixer and shaped by using a mold to obtain a lip gloss product using the ester oil according to the present invention.

Cosmetic Agent Formulation Example 10

In this example, the ester oil according to the present invention is used to a formulation of lipstick. The formulation is as follows.

Candelilla wax, carnuba wax, multiwax, dipentaerythritol hexahydroxy stearate, polybutene, sorbitan olivate, Arlacel 83, jojoba oil, meadowfoam seed oil, diisostearyl maleate, isononyl isononanoate, triethylhexanoin, castor oil, polymethyl methacrylate, pigments, pearlescent agents and the ester oil according to the present invention are mixed and dissolved at 75-80° C., followed by dispersion with a homomixer. Then, a fragrance is added thereto and the resultant mixture is shaped by using a mold to obtain a lipstick product using the ester oil according to the present invention.

INDUSTRIAL APPLICABILITY

The ester oil according to the present invention has a higher moisturizing effect than silicone oil, provides a light feel of use, and increases the viscosity of a cosmetic agent to impart stability thereto. Therefore, the ester oil can partially or totally substitute silicone oil commercialized due to the disadvantages of the conventional synthetic ester oil, and thus allows a cosmetic composition to have more human-friendly naturally occurring ester oil as a base ingredient.

The invention claimed is:

1. A cosmetic composition comprising, as an active ingredient, ester oil obtained by mixing and esterification of amyl alcohol or an isomer thereof with fatty acids derived from natural vegetable oil.

2. The cosmetic composition according to claim 1, wherein the isomer is any one isomer selected from the group consisting of 3-methyl-1-butanol(isoamyl alcohol), 2-methyl-1-butanol, 2,2-dimethyl-1-propanol, 3-pentanol, 2-pentanol, 3-methyl-2-butanol, and 2-methyl-2-butanol.

3. The cosmetic composition according to claim 1, wherein the natural vegetable oil is olive oil or coconut oil.

4. The cosmetic composition according to claim 3, wherein the fatty acids derived from olive oil is at least one selected from the group consisting of palmitic acid, palmitoleic acid, stearic acid, oleic acid, linoleic acid and linolenic acid.

5. The cosmetic composition according to claim 3, wherein the fatty acids derived from coconut oil is at least one selected from the group consisting of caprylic acid, capric acid, lauric acid, myristic acid, palmitic acid, stearic acid and oleic acid.

6. The cosmetic composition according to claim 1, wherein the fatty acids derived from natural vegetable oil is a mixture of fatty acids extracted from natural vegetable oil by using a high-temperature high-pressure method.

7. The cosmetic composition according to claim 1, wherein the ester oil is at least one isoamyl olivate selected from the following Structural Formulae 15-20:

Isoamyl palmitate

[Structural Formula 15]

Isoamyl palmitoleate

[Structural Formula 16]

8. The cosmetic composition according to claim 1, wherein the ester oil is at least one isoamyl cocoate selected from the following Structural Formulae 21-27:

-continued

[Structural Formula 27]

Isoamyl oleate

9. The cosmetic composition according to claim 1, which has a skin moisturizing effect and an effect of thickening cosmetic agents.

10. A cosmetic product comprising the cosmetic composition as defined in claim 1 as base oil.

11. The cosmetic product according to claim 10, which is lotion, cream, serum, foundation, sun cream, BB cream, makeup base, lip gloss or lipstick.

* * * * *